US008704045B2

(12) United States Patent
Watson

(10) Patent No.: US 8,704,045 B2
(45) Date of Patent: Apr. 22, 2014

(54) ONIONS WITH HIGH STORAGE ABILITY, HIGH SOLUBLE SOLIDS CONTENT AND/OR LOW PUNGENCY

(75) Inventor: Rick Watson, Brooks, OR (US)

(73) Assignee: Nunhems B.V., Nunhem (NL)

( * ) Notice: Subject to any disclaimer, the term of this patent is extended or adjusted under 35 U.S.C. 154(b) by 77 days.

(21) Appl. No.: 13/287,088

(22) Filed: Nov. 1, 2011

(65) Prior Publication Data

US 2012/0045565 A1    Feb. 23, 2012

Related U.S. Application Data

(63) Continuation-in-part of application No. 12/861,740, filed on Aug. 23, 2010, which is a continuation-in-part of application No. 12/020,360, filed on Jan. 25, 2008, now abandoned.

(51) Int. Cl.
| | | |
|---|---|---|
| *A01H 5/00* | (2006.01) | |
| *A01H 4/00* | (2006.01) | |
| *A01H 5/02* | (2006.01) | |
| *A01H 5/04* | (2006.01) | |
| *A01H 5/06* | (2006.01) | |
| *A01H 5/08* | (2006.01) | |
| *A01H 5/10* | (2006.01) | |
| *A01H 5/12* | (2006.01) | |
| *A01H 1/00* | (2006.01) | |
| *A01H 1/02* | (2006.01) | |

(52) U.S. Cl.
USPC ........... 800/298; 800/295; 800/303; 800/260; 800/263; 800/274; 435/419

(58) Field of Classification Search
None
See application file for complete search history.

(56) References Cited

U.S. PATENT DOCUMENTS

| | | | | |
|---|---|---|---|---|
| 2007/0016984 | A1* | 1/2007 | Hendricks | 800/295 |
| 2008/0014329 | A1* | 1/2008 | Hendricks | 426/638 |
| 2010/0319081 | A1* | 12/2010 | Watson | 800/260 |
| 2011/0041217 | A1* | 2/2011 | Watson | 800/298 |

FOREIGN PATENT DOCUMENTS

WO    WO 2007/011857    1/2007

OTHER PUBLICATIONS

Lancaster et al. Does sulphur supply to the bulb affect storage of onions. (2001) Acta Horticulture 555; pp. 111-115.*
Havey et al. Significant variation exists among laboratories measuring onion bulb quality traits. (2002) HortScience; vol. 37; pp. 1086-1087.*
Alan et al. Fecund gynogenic lines from onion (*Allium cepa* L.) breeding materials. (2004) Plant Science; vol. 167; pp. 1055-1066.*
Havey et al. Combining abilities for yield and bulb quality among Long- and Intermediate-day open-pollinated onion populations. (1996) J. Amer. Soc. Hort. Sci.; vol. 121; pp. 604-608.*
Havey, M. J. The USDA onion-breeding program: new releases and new directions. (1998) National Onion Research Conference.*
Simon, P. W. Genetic analysis of pungency and soluble solids in long-storage onions. (1995) Euphytica; vol. 82; pp. 1-8.*
Schwimmer et al. (1962) Journal of Food Science 27(1): 94-97.
Simon (1995) Euphytica 82(1): 1-8.
Wall et al. (1996) Euphytica 87(2): 133-139.
Wall et al. (1992) HortScience 27(9): 1029-1030.
Dhumal et al (2007) Food Chemistry 100(4): 1328-1330.
Foskett and Peterson (1949) Proceedings of the American Society for Horticultural Science 55: 314-318.
Galmarini et al. (2001) Molecular Genetics and Genomics 265: 543-551.
Havey et al. (2004) Genome 47: 463-468.
Lin (1995) Journal of the American Society for Horticultural Science 120: 119-122.
MacCallum et al (2001) New Zealand Journal of Crop and Horticultural Science 29: 149-158.
MacCallum et al. (2006) Theoretical and Applied Genetics 114(5): 815-822.
Mann and Hoyle (1945) Proceedings of the American Society for Horticultural Science 46: 285-292.
Randle (1992) Euphytica 59: 151-156.
Randle and Bussard (1993) Journal of American Society Horticultural Science 118(6): 766-770.
Schwimmer and Guadagni (1961) Journal of Food Science 27: 94-97.
Shock et al. (2004) "Pungency of Selected Onion Varieties Before and After Storage," Oregon State University, Malheur Experiment Station Special Report 1055: 45-46.
Wall and Corgan (1999) Euphytica 106: 7-13.

* cited by examiner

*Primary Examiner* — Cathy Kingdon Worley
(74) *Attorney, Agent, or Firm* — Hunton & Williams LLP

(57) ABSTRACT

Long-day onion plants, capable of producing onion bulbs comprising 'high soluble solids' combined with a 'sweet taste' as a result of low pungency, are provided, as are methods for producing such plants, bulbs and seeds. Such onions can be stored for long periods without a loss in quality and without an increase in pungency.

16 Claims, No Drawings

ONIONS WITH HIGH STORAGE ABILITY, HIGH SOLUBLE SOLIDS CONTENT AND/OR LOW PUNGENCY

CROSS-REFERENCE TO RELATED APPLICATIONS

This application is a Continuation-in-Part of U.S. patent application Ser. No. 12/861,740, filed Aug. 23, 2010, which is a Continuation-in-Part of U.S. patent application Ser. No. 12/020,360, filed Jan. 25, 2008, now abandoned, the disclosures of both of which are hereby incorporated by reference in their entirety.

FIELD OF THE INVENTION

The invention relates to plant breeding and plant improvement, in particular plants of the species *Allium cepa* (onion) having new quality characteristics and combinations of at least two characteristics selected from 'high soluble solids content', 'low pungency' (LP) and/or 'long storage' (LS), essentially without significant quality loss during storage (e.g., no significant increase in pungency and/or no significant reduction in soluble solid content). Provided are onion bulbs, plants and seeds having these characteristics (both open pollinated and hybrids, especially long-day onions) as well as methods for making these.

BACKGROUND OF THE INVENTION

The onion plant is believed to originate from West or Central Asia. In Europe it has been known since the bronze ages. The bulbs of the onion plants,—the "onions"— are used in many dishes and have a very healthy reputation. Plant breeding has been focused on yield, appearance, harvestability, storability, flavor and content as onions contain several compounds that have beneficial effects on health. Some of these compounds are most effective when the onion is consumed fresh and their concentrations are often linked with the solids level of onions. A high solids onion that is mild and sweet enough to be consumed without cooking will deliver more health promoting compounds in the diet.

Onion varieties are characterized by day length; "long-day" onion varieties will stop forming tops and begin to form bulbs when the day length reaches 14 to 16 hours while "short-day" onions will start making bulbs in early spring or in autumn/winter when there are only 10 to 12 hours of daylight. "Long-day" onions are usually produced in northern countries or northern states of the USA (north of the 36th parallel; especially latitude) 38°-48° while "short-day" onions are produced in countries or states south of that line (especially below latitude 32°). Long-day onion varieties generally have a more pungent flavor than short-day varieties, which are sweet. Long-day varieties also store better and longer than short-day varieties because they have a relatively higher dry matter content or higher percentage of soluble solids (SSC) compared to short-day onions (see e.g., "Onion Planting" publication, obtainable from the Texas A&M University horticulture website The long storage ability of long-day onion varieties provides the possibility to market onions during late summer, fall and winter (August-March/April) when mild, short-day onions are not available or scarce. Long-day onions are bi-annual for seed production. Seeding for seed production purposes occurs in autumn, possibly, but not necessarily, followed by transplanting in spring. Seed is harvested the next summer. For bulb production long-day onions are seeded early spring, harvested in autumn and subsequently stored over winter. Short-day onions can be seeded in autumn and harvested in spring the next year, or seeded in spring and harvested in early summer of the same year. As the storage ability of short-day onions is low, the availability of these mild onions is restricted to spring-early summer (April-July).

Pungency is the typical onion flavor or taste, caused by the conversion of sulphur containing flavor precursors—alk(en)yl-L-cysteine-sulfoxides (ACSOs)—by the enzyme allinase into thiosulfonates when the onion cells are cut or damaged. A by-product of this enzymatic process, pyruvate or pyruvatic acid is measured as an indicator of the pungency (Schwimmer and Weston 1961, J. of Agric. Food Chem. 9: 301-4). The amount of pyruvate produced is directly related to onion pungency as determined by taste panels (Schwimmer and Guadagni, 1962, J. Food Sc. 27:94-97).

Pungency is an important commercial trait as consumers favour fresh onions with low pungency and sweet taste. Pungency masks the sweet taste of the sugars, which are present in the onion as part of the water-soluble solids or carbohydrates. Pungency is strongly influenced by the presence or absence of sulphur in the soil or plant nutrients (Randle 1992, Euphytica 59: 151-156 and Randle and Bussard 1993, J. Amer. Soc. Hort. Sci. 118: 766-770), but has also a clear genetic component as shown by Lin (1995, J. Americ. Soc. Hort. Sci. 120: 119-122), Simon (1995, Euphytica 82: 1-8), Wall et al. (1996, Euphytica 87: 133-139) and Wall and Corgan (1999, Euphytica 106: 7-13). Pungency can, therefore, vary between locations and between years.

Dry matter in onions consists of both soluble and insoluble carbohydrates. The soluble solids are in the form of fructose, sucrose, glucose, fructans and other saccharides. The analysis of dry matter can be time consuming and destructive for the bulbs. Several researchers have determined that dry matter content and refractive index (soluble solids content) are positively correlated with the percentage of dry matter and the refractive index determination avoids destruction of the bulbs (Mann and Hoyle, 1945, Proc. Americ. Soc. Hort Sci. 46: 285-292; Foskett and Peterson, 1949, Proc. Americ. Soc. Hort Sci. 55: 314-318). Low pungency in onions is strongly correlated with low dry matter content or a low percentage of soluble solids (see further below). Short-day onions, thus, have a low pungency and a low SSC at harvest, and cannot be stored for long periods. For the fresh onion market in northern countries or northern states of the USA (i.e., for long-day countries), however, there is a long existing need for low pungency varieties. This requires long-day onions that combine the properties 'low pungency' with 'high solids'. Such onions do not yet exist in the art, because there is an alleged genetic linkage between the properties 'high pungency' and 'high (soluble) solids'. Thus, long-day onions have a high pungency and a high SSC, whereby they can be stored throughout the winter.

This linkage between high pungency and high SSC is, for example, illustrated by a study of Galmarini et al. (2001, Mol. Gent. Genomics 265: 543-551) wherein molecular markers which were significant for pungency were also significant for SSC, suggesting that this characteristic may be controlled by the same chromosome region. It implies a genetic linkage or association between these traits, resulting in short-day onions, which generally have a low soluble solid content together with a low pungency and long-day onions having a high soluble solid content combined with high pungency.

Also other studies support the strong linkage between the two traits—SSC and pungency (Schwimmer and Weston, 1961, supra; Randle 1992, supra; Simon 1995 supra; Lin 1995; MacCallum et al. 2001, NZ J. of Crop and Hort. Sci. 29:

149-158; Galmarini 2001, supra). For example Simon (1995, supra) observes a strong correlation between pungency and SSC in the parent lines, the F1, F2 and BC1 generations of a diallel between 4 parent inbred lines. Galmarini et al. (2001, supra) and Havey et al. (2004, Genome 47: 463-468) found a phenotypic and genetic significant positive correlation between solids and pungency in the F3 generation.

Galmarini et al. and Havey et al. suggest that this linkage may be the result of pleiotropic effects. There is physiological evidence for this scenario as the higher accumulation of fructans in high solids onions, because of no hydrolization of fructans to fructose and less water uptake, is associated with greater thiosulfinate concentrations, yielding strong correlations among soluble carbohydrates, pungency and onion-induced in vitro anti platelet activity (OIAA). The increase in water content and free fructose in low solids onions could be responsible for diluting the compounds related to pungency and increase the sweeter and milder taste. The QTL analysis as discussed in these articles shows a strong linkage in one group (E) between dry matter percentage (DM %), pungency and OIAA, while DM % and solids are strongly linked in a different group (D). This implies a strong association between DM %, soluble solids, pungency and OIAA, which would be difficult to overcome.

According to some reports (Shock et al. 2004: "Pungency of Selected Onion Varieties Before and After Storage", Oregon State University, Malheur Experiment Station Special Report 1055: 45-46) pungency may significantly increase during storage. There is, therefore, a need for onions which have a low pungency and high SSC at harvest and whereby the pungency does not increase significantly during storage. In particular, there is a need for onions which have a low pungency and high SSC at harvest, and a low pungency and high SSC after at least about 2, 3, 4, 5, 6, 7, 8 or more months of storage. There is especially a need for low pungency long day onions whereby the pungency does not increase during storage but remains constant or decreases during storage (compared to the level at harvest), i.e. is lower after at least about 2, 3, 4, 5, 6, 7, 8 or more months of storage compared to the level at harvest. A "decrease during storage" refers, thus, to the level after a specific period of storage (e.g. after about 2, 3, 4, 5, 6, 7, 8 or more months of storage) is lower than at harvest. For example if the mean PAD measurement at harvest is 4.92 and after about 3 months is 4.62, then the level has decreased during the 3 months storage period.

SUMMARY OF PREFERRED EMBODIMENTS OF THE INVENTION

The invention provides for an onion plant requiring 14 or more contiguous hours of daylight to initiate bulb formation comprising a bulb having low pungency, particularly such onion plant, wherein said bulb has a PAD measurement at harvest of less than 5.5 µM/g FW pyruvate, less than 5.0 µM/g FW pyruvate, less than 4.5 µM/g FW pyruvate, less than 4.0 µM/g FW pyruvate, less than 3.75 µM/g FW pyruvate, or equal to or less than 3.5 µM/g FW pyruvate. Provided are onion plants wherein the bulbs maintain this low pyruvate level during at least about 2, 3, 4, 5, 6, 7, or 8 months of storage, or wherein the pyruvate level decreases further during storage compared to the level at harvest. Thus, the bulbs have a (mean) lower PAD measurement after at least about 2, 3, 4, 5, 6, 7 or 8 months of storage compared to the (mean) PAD measurement at harvest. In one embodiment the mean PAD measurement (pungency) after about 2, 3, 4, 5, 6, 7, 8, or more, months of storage is equal to or less than 5.0, 4.5, 4.0, 3.75, 3.5 µM/g FW pyruvate, or equal to or less than 3.0, 2.8, 2.5, 2.3, 2.0, 1.8, 1.4 µM/g FW pyruvate or equal to or less than 1.3 µM/g FW pyruvate.

Also provided herein is any one of the above onion plants, wherein said onion plant is a yellow, red, brown or white onion (bulb color) and/or a Spanish-type or other type onion (Hard Globe Eastern Type, Hard Globe Western Type, Northern Yellow Type). Further provided herein is any one of the above onion plants, wherein said bulb is low pungent at harvest, or wherein said bulb substantially maintains low pungency after storage for about 2 months or more, such as any of the above onion plants, wherein a PAD measurement after storage is increased less than 10% from a PAD measurement at harvest, preferably wherein the PAD measurement after storage for 2, 3, 4, 5, 6, 7, 8 or more months is 98%, 95%, 93%, 90%, 85%, 80% or less of the PAD measurement at harvest, wherein said bulb substantially maintains low pungency after storage for about 4 months, or wherein a PAD measurement after storage is increased less than 10% from a PAD measurement at harvest.

Further provided is any one of the above onion plants and bulbs produced by the plants, wherein said bulb substantially maintains low pungency after storage for about 6 months, such as any one of the above onion plants, wherein a PAD measurement after storage is increased less than 10% from a PAD measurement at harvest, more preferably wherein the mean PAD measurement after 4, 5, or 6 months of storage is significantly lower than at harvest. Also provided herein is any one of the above onion plants, wherein said onion plant requires 14 or more contiguous hours of light for 2 or more, 4 or more, or 7 or more days to initiate bulb formation.

In accordance with this invention, provided herein is a part of an onion plant requiring 14 or more contiguous hours of light to initiate bulb formation, wherein said plant comprises a bulb having a PAD measurement of less than 5.5 µM/g FW pyruvate, or even less than or equal to 3.5 µM/g FW pyruvate, such as a plant part, which is selected from the group consisting of a seed or seed-part, a bulb or a bulb-part, a leaf or leaf part, pollen, or an ovule.

Further provided herein is a cell, a protoplast, or a tissue culture of cells derived or obtained from any one of the above onion plants and bulbs, such as a tissue culture from a tissue selected from the group consisting of leaf, pollen, embryo, bulb, anther, flower, bud, and meristem.

Also provided herein is a long-day onion plant comprising a bulb having low pungency, such as a yellow, red, brown or white onion or a Spanish-type onion plant comprising a bulb having low pungency.

Further provided herein is an onion bulb from a onion plant requiring 14 or more contiguous hours of light to initiate bulb formation comprising a PAD measurement less than about 5.5 µM/g FW pyruvate, less than about 5.0 µM/g FW pyruvate, less than about 4.5 µM/g FW pyruvate, less than about 4.0 µM/g FW pyruvate, less than about 3.75 µM/g FW pyruvate, or equal to or less than 3.5 µM/g FW pyruvate, or equal to or less than 3.0 or 2.5 µM/g FW pyruvate at harvest, and/or after 2, 3, 4, 5, 6, 7, or more months of storage, such as any one of said bulbs which is a yellow, red or white onion bulb, or a Spanish onion bulb.

Also provided herein is a container of onion bulbs from onion plants requiring 14 or more contiguous hours of light to initiate bulb formation comprising an average PAD measurement of less than about 5.5 µM/g FW pyruvate, less than about 5.0 µM/g FW pyruvate, less than about 4.5 µM/g FW pyruvate, or less than or equal to 3.5 µM/g FW pyruvate, or less than or equal to 3.0 or 2.5 µM/g FW pyruvate at harvest, and/or after 2, 3, 4, 5, 6, 7, or more months of storage. Further provided is any such container, wherein at least 75%, at least 85%, or at least 95% of said onion bulbs have a PAD measurement of less than about 5.5 µM/g FW pyruvate. Included herein is any one of the above containers, wherein said container is selected from a bag, a can, a box, and a flat, or a container that contains 1 pound or 5 pounds of onion bulbs. Further included herein is any one of the above containers, wherein said container is in a store, such as a grocery store.

The invention also provides a seed of an onion plant requiring 14 or more contiguous hours of light to initiate bulb formation, wherein said seed is capable of producing an onion plant having a bulb comprising a PAD measurement of less than about 5.5 µM/g FW pyruvate, less than about 5.0 µM/g FW pyruvate, less than about 4.5 µM/g FW pyruvate, less than about 4.0 µM/g FW pyruvate, or equal to or less than 3.5 µM/g FW pyruvate, or equal to or less than 3.0 or 2.5 µM/g FW pyruvate at harvest, and/or after 2, 3, 4, 5, 6, 7, or more months of storage.

Also provided herein is a container of seeds of an onion plant requiring 14 or more contiguous hours of light to initiate bulb formation wherein onion bulbs from greater than 50% of said seeds are low pungency onions, wherein a population of onion bulbs from said seeds contain an average PAD measurement of less than about 5.5 µM/g FW pyruvate, or less than about 5.0 µM/g FW pyruvate, less than about 4.5 µM/g FW pyruvate, less than about 4.0 µM/g FW pyruvate, or equal to or less than 3.5 µM/g FW pyruvate, or equal to or less than 3.0 or 2.5 µM/g FW pyruvate at harvest, and/or after 2, 3, 4, 5, 6, 7, or more months of storage, such as a container which comprises at least 100 or 1000 seeds. Such container can be a bag, a box, or a packet. Further provided herein is a any one of the above container of seeds, wherein bulbs from greater than 75%, greater than 85% or 95%, or greater than 98%, of said seeds are low pungency onions.

Also provided herein is a method of producing a hybrid onion seed comprising: crossing a low pungency onion plant requiring 14 or more hours of light to initiate bulb formation with another onion plant; and obtaining F1 onion seed. Further provided herein is such method, wherein said low pungency onion is an onion line designated I37853B, I37554A, or I37554B, deposited under ATCC Accession Nos. PTA-9053, PTA-9054 and PTA-9055, respectively.

The invention also provides a seed of I37853B, a sample of said seed having been deposited under ATCC Accession No. PTA-9053, an onion plant grown from said seed, an onion plant part from such onion plant, such as pollen, protoplast, an ovule, or a cell. Also provided herein is a tissue culture of cells obtained from said plant, such as a tissue culture of cells from a tissue selected from the group consisting of leaf, pollen, embryo, bulb, anther, flower, bud, and meristem.

Also provided herein is seed of I37554A or B, a sample of said seed having been deposited under ATCC Accession No. PTA-9054 and PTA-9055, respectively, an onion plant grown from any one of said seed, an onion plant part from any one of said onion plants, such as pollen, protoplast, an ovule, or a cell. Also provided herein is a tissue culture of cells obtained from any one of said plants, such as a tissue culture of cells from a tissue selected from the group consisting of leaf, pollen, embryo, bulb, anther, flower, bud, and meristem.

Further provided herein is a hybrid onion plant having a bulb comprising a PAD measurement of less than about 5.5 µM/g FW pyruvate, or even less than or about 4.5 µM/g FW pyruvate, less than about 4.0 µM/g FW pyruvate, or equal to or less than 3.5 µM/g FW pyruvate, or equal to or less than 3.0 or 2.5 µM/g FW pyruvate at harvest, and/or after 2, 3, 4, 5, 6, 7, or more months of storage.

Also provided herein is a long-day onion plant producing bulbs which have a mean PAD measurement at harvest of less than 3.75 µM/g fresh weight (FW) pyruvate, or equal to or less than 3.5 µM/g FW pyruvate, or equal to or less than 3.0 or 2.5 µM/g FW pyruvate (at harvest, and/or after 2, 3, 4, 5, 6, 7, or more months of storage), such as any one of said onion plants, wherein said bulbs have a mean soluble solids content (SSC) at harvest of at least 7.0%, at least 7.5%, or at least 8%. Preferably the mean SSC content after 2, 3, 4, 5, 6, 7, or more months of storage is high, e.g. at least 7.0%, 7.2%, 7.4%, 7.5%, 7.8%, 8.0%, or more.

Further provided herein is any of the above onion plants, wherein said PAD measurement is increased by less than 10% after storage for at least 4 months compared to the PAD measurement at harvest, and such or any of the above onion plants, wherein said SSC is reduced by less than 2% after storage for at least 4 months.

Also provided herein is any one of the above onion plants producing bulbs wherein the pungency level of the most pungent bulb and least pungent bulb differ by at most 5 µMol/g FW, or by at most 3.5 µMol/g FW, or such or any one of the above onion plants producing bulbs wherein all bulbs have a pungency between 0 and 5 µMol/g FW, between 1 and 5 or between 1 and 4 µMol/g FW.

Further provided herein is any of the above onion plants, wherein said onion plant requires 14 or more contiguous hours of light for 2 or more days to initiate bulb formation, such as such onion plant or any one of the above onion plants of the invention, wherein said mean PAD or mean SSC is obtained from at least 10 onion bulbs of said plant.

Also provided in accordance with the invention is any one of the above onion plants, wherein said plant is a hybrid, or is a plant derivable or obtainable from a line designated I37853B, I37554A, or I37554B, deposited under ATCC Accession Nos. PTA-9053, PTA-9054 and PTA-9055, respectively.

Further provided herein are seeds or bulbs of any one of the above onion plants, and a container comprising a plurality of such or any one of the above bulbs, such as a any such container, wherein at least 75% of the bulbs are bulbs according to the invention. Also provided herein is any one of the above containers, wherein said container comprises at least 1 pound of bulbs according to the invention.

Also set forth herein is a part of any of the above onion plants, or of any one of the above seeds or bulbs, such as a part a cell or cell culture, a tissue culture, a protoplast or a plant organ.

Hence, in one aspect, the invention provides long day onion plants which produce bulbs having low pungency but high SSC and/or which can be stored for at least 2, 3, 4, 5, 6, 7 months or more without any significant increase in pungency (compared to the level at harvest) and/or without any significant reduction in SSC (compared to the level at harvest). It is a further object to provide a plurality of long day plants, seeds from these plants, bulbs and containers with any of these and methods of making long day onion plants having these phenotypic characteristics.

In another aspect, the invention provides an onion plant requiring 14 or more contiguous hours of daylight to initiate bulb formation comprising a bulb having low pungency. In another aspect, the invention provides an onion plant requiring 14 or more contiguous hours of light for 2, 4, 7 or more days to initiate bulb formation. The invention provides for yellow, Spanish and other types of onion plants. The invention also provides for cells, protoplasts and tissue cultures from the plants (or plant cells) of the invention.

In a further aspect, the bulb has a mean PAD measurement at harvest of less than 5.5, 5.0, 4.5, 4.0, 3.8, 3.75 or 3.5 µM/g FW pyruvate. In another aspect, the bulb has a mean PAD measurement at harvest of 3.5 µM/g FW pyruvate, or less. In another aspect, the bulb is low pungent at harvest. In another aspect, the bulb substantially maintains low pungency after storage for about 2, 4 or 6 months. In another aspect the pungency and mean PAD measurement decreases during 2, 4, 5, 6, 7 or more months of storage relative to the level at harvest, i.e. is lower than at harvest and is about 4.5 µM/g FW pyruvate or less, less than about 4.0 µM/g FW pyruvate, or equal to or less than 3.5 µM/g FW pyruvate, or equal to or less than 3.0, 2.5 or 2.3 µM/g FW pyruvate. In another aspect, the PAD measurement after storage for 2, 4 or 6 months is increased less than 10% from a PAD measurement at harvest.

In another aspect, the invention provides a part of an onion plant requiring 14 or more contiguous hours of light to initiate bulb formation, wherein said plant comprises a bulb having a PAD measurement of less than 5.5 µM/g FW pyruvate, or even less than or equal to 3.5 µM/g FW pyruvate, or less. The plant part may be a seed, bulb, leaf, pollen or an ovule.

In another aspect, the invention provides a container of onion bulbs from onion plants requiring 14 or more contiguous hours of light to initiate bulb formation comprising an average PAD measurement of less than about 5.5, 5.0, 4.5, 4.0, 3.75 or 3.5 µM/g FW pyruvate, or equal to or less than 3.5, 3.0, 2.5 or 2.3 µM/g FW pyruvate. In another aspect, the invention provides that at least 75, 85 or 95% of onion bulbs in a container have a PAD measurement of less than about 5.5 µM/g FW pyruvate.

In another aspect, the invention provides a seed of an onion plant requiring 14 or more contiguous hours of light to initiate bulb formation, wherein said seed is capable of producing an onion plant having a bulb comprising a PAD measurement of less than about 5.5, 5.0, 4.5, 4.0, 3.75 or 3.5 µM/g FW pyruvate, or equal to 3.5 µM/g FW pyruvate. The invention also provides for a container of seeds, wherein onion bulbs from greater than 50% of said seeds are low pungency onions.

In another aspect, the invention provides a method of producing a hybrid onion seed comprising: crossing a low pungency onion plant requiring 14 or more hours of light to initiate bulb formation with another onion plant; and obtaining F1 onion seed. In another aspect, the invention provides low pungency onion lines designated I37853 or I37554, seeds from these onion lines, plants grown from these seeds and plant parts and tissues from these plants.

In another aspect, the invention provides a hybrid onion plant having a bulb comprising a mean PAD measurement of less than about 5.5 or 3.5 µM/g FW pyruvate, or equal to 3.5 µM/g FW pyruvate or equal to or less than 3.5, 3.0, 2.5 or 2.3 µM/g FW pyruvate at harvest and/or after 3, 4, 5, 6, 7 or more months of storage. Also hybrid seeds and bulbs are provided herein.

In another aspect, the invention provides onions having high SSC, good storage ability and low pungency.

DETAILED DESCRIPTION OF PREFERRED EMBODIMENTS OF INVENTION

Definitions

As used herein, the phrase "to comprise" and its conjugations is used in its non-limiting sense to mean that items following the word are included, but items not specifically mentioned are not excluded. In addition, reference to an element by the recitation of "a" or "an" does not exclude the possibility that more than one of the element is present, unless the context clearly requires that there be one and only one of the elements. Thus, "a" or "an" usually means "at least one", e.g., "a cell" refers also to several cells in the form of cell cultures, tissues, whole organism, etc. Similarly, "a bulb" or "a plant" also refers to a plurality of bulbs and plants, respectively.

As used herein, the term "plant" includes the whole plant or any parts or derivatives thereof, such as plant organs (e.g., harvested or non-harvested storage organs, bulbs, tubers, fruits, leaves, etc.), plant cells, plant protoplasts, plant cell tissue cultures from which whole plants can be regenerated, plant calli, plant cell clumps, and plant cells that are intact in plants, or parts of plants, such as embryos, pollen, ovules, fruits (e.g., harvested tissues or organs), flowers, leaves, seeds, tubers, bulbs, clonally propagated plants, roots, stems, root tips and the like. Also any developmental stage is included, such as seedlings, immature and mature bulbs, etc.

"Variety" means a plant grouping within a single botanical taxon of the lowest known rank, which grouping, irrespective of whether the conditions for the grant of a breeder's right are fully met, can be defined by the expression of the characteristics resulting from a given genotype or combination of genotypes, distinguished from any other plant grouping by the expression of at least one of the said characteristics and considered as a unit with regard to its suitability for being propagated unchanged.

"Phenotype" is the observable external and/or physiological appearance of the plant as a result of the interaction between its genotype and its environment. It includes all observable morphological and physiological characteristics and thus encompasses phenotypes such as pungency, PAD measurements and soluble solid contents of onion bulbs.

"Genotype" is the total of inheritable genetic information of a plant, partly influenced by the environmental factors, which is expressed in the phenotype.

As used herein, "Onion plant" or "onion" is a plant of the botanical species *Allium cepa* L. or parts thereof, such as the (harvested) bulb, seeds, etc. "Bulb" is the harvested, edible portion of the plant. Onion bulbs may be developing or mature. Herein mature bulbs are preferred, which are bulbs ready for harvest or harvested.

"Long-day" onion plants will initiate bulb formation when light (day length) is at least about 14 contiguous hours or more, e.g., at least about 14, 15 or 16 hours. Preferably this contiguous light (hours per day) is provided for 2, 4, 7, 14, 21, 25 or more days to initiate bulb formation.

"Storage conditions" and "storage" encompass typical conditions used to store (preferably fresh) onions, such as darkness, cool temperature (as used herein, a cool temperature means preferably below 12° C., e.g., about 3-12° C., 3-10° C., 5-10° C. or about 3-5° C., preferably about 3, 4 or 5 degrees Celsius) and a relative humidity (RH) of about 60-80%, preferably about 70-80%, most preferably around 70%. Also preferred is controlled ventilation.

A "family" is the progeny of one plant, which has been pollinated by a number of different other plants.

"Hybrid" or "hybrid plant" is a plant produced by the inter-crossing (cross-fertilization) of at least two different plants or plants of different parent lines. It is understood that the seeds of such a cross (hybrid seeds) are encompassed herein, as well as the hybrid plants grown from those seeds and plant parts derived from those grown plants (e.g. bulbs).

"F1, F2, etc." refers to the consecutive related generations following a cross between two parent plants or parent lines. The plants grown from the seeds produced by crossing two plants or lines is called the F1 generation. Selfing the F1 plants results in the F2 generation, etc.

"Soluble Solids" or "Soluble Solids Content" ("SSC" herein), is the percentage (%) of water-soluble compounds in onion bulbs as measured by a refractometer according to the method of Mann and Hoyle, 1945 (Proc. Americ. Soc. Hort. Sci. 46: 285-292) or Foskett and Peterson, 1949 (Proc. Americ. Soc. Hort. Sci. 55: 314-318).

"High SSC" refers herein to an average SSC of a representative number of onion bulbs (e.g., at least 5, 6, 10, 15, 20, 30, 40, 50, 50, 60, 70, 80, 90 or more bulbs) of at least 7.0% or 7.5%, or even at least 8%, 9%, 10%, 11%, 12%, 15%, 20%, 25%, 30% or more. Thus, average SSC of 7.0-30%, 7.5-30%, or even 7.0-20%, 8.0-20%, 7.0-15%, 8.0-15%, 7.0-10%, etc. are encompassed herein. Throughout this document "average" and "mean" are used interchangeably and refer to the arithmetic mean.

"Pungency" is the typical sharp taste of onion as the onion bulb tissue disintegrates by comminution. Pungency is preferably determined by measuring the enzymatic development of pyruvic acid according to the method of Schwimmer and Weston (1961, J. of Agric. Food Chemistry 9:301-304), which is strongly correlated to the flavor perception by a test panel (Schwimmer 1962, J. Food Sci. 27: 94-97; Wall and Corgan, 1992, Hort. Science 27: 1029-1030). Pungency is expressed as $\mu$Mol (micromoles, also $\mu$M or $\mu$mol herein) per gram fresh weight bulb material ($\mu$Mol/g FW). It is also referred to as "PAD measurement" (PAD from Pyruvic Acid Development) or "pyruvate measurement" or "pyruvate level" herein.

"Low pungency" refers herein to an average pungency of a representative number of (mature) onion bulbs (e.g., at least about 5, 8, 10, 15, 20, 30, 40, 50, 50, 60, 70, 80, 90 or more bulbs) of less than 5.5 $\mu$Mol/g FW, or even less than 5.0, 4.5, 4.0 $\mu$Mol/g FW, equal to or less than 3.8 or 3.75 $\mu$Mol/g FW, or equal to or less than 3.5, 3.0, 2.5, 2.3, 2.0, 1.8, 1.5, or 1.3 $\mu$Mol/g FW, as determined by PAD measurement. Thus, average pungencies of between 3.5 and 1.3 $\mu$Mol/g FW, between 3.0 and 1.3 $\mu$Mol/g FW, or between 3.0 and 2.0 $\mu$Mol/g FW, etc. are encompassed herein. Pungency can be measured at harvest and/or after 2, 3, 4, 5, 6, 7, 8 or more months of storage.

A "narrow pungency range" refers to the variance in pungency between individual bulbs of a plurality of bulbs obtained from one plant line being narrow, i.e., the pungency level of the most pungent bulb (maximum value) and least pungent bulb (minimum value) differ preferably by less than or at most 5 $\mu$Mol/g FW, more preferably less than or at most 4 $\mu$Mol/g FW or less than or at most 3.5 $\mu$Mol/g FW, more preferably by less than or at most 3.0, 2.5, 2.0, 1.5 or 1.0 $\mu$Mol/g FW. Preferably the maximum pungency (of the most pungent bulb produced by the plant) is equal to or less than 5 $\mu$Mol/g FW, preferably equal to or less than 4.9, 4.8, 4.75, 4.7, 4.5, 4.0 or 3.8, 3.7, 3.5 or 3.0 $\mu$Mol/g FW. Preferably the minimum pungency level (i.e. of the least pungent bulb produced by the plant) is equal to or below 3.0, 2.5, more preferably equal to or below 2.0, 1.3 or 1.2 $\mu$Mol/g FW. Preferred ranges of pungency within a plant line are, thus, that all bulbs have a pungency between 0 (min) and 5 (max) $\mu$Mol/g FW, preferably between 1 (min) and 5 (max) $\mu$Mol/g FW, more preferably between 1 (min) and 4 (max) $\mu$Mol/g FW. Also, in one embodiment of the invention, all bulbs have a pungency between 0 (min) and 5 (max) $\mu$Mol/g FW, preferably between 1 (min) and 5 (max) $\mu$Mol/g FW, more preferably between 1 or 1.2 (min) and 4.9, 4.8, 4.7 or 4.5 (max) $\mu$Mol/g FW, more preferably between 1 (min) and 4 (max) $\mu$Mol/g FW. A narrow pungency range is an important quality characteristic for the consumer. It can be measured at harvest and/or, preferably, after a certain period of storage, e.g. after at least about 2, 3, 4, 5, 6, 7, 8 or more months of storage.

"Long storage" refers herein to a storage length of at least 2, 3, 4, 5, 6, 7 or more months. Preferably there is no significant increase in pungency and/or no significant reduction in SSC during the storage period, i.e., when comparing the average pungency and/or SSC at harvest (or shortly after harvest) with the pungency and/or SSC level after 2, 3, 4, 5, 6, 7 or more months of storage. "No significant increase in pungency" refers herein to an increase in pungency measurement (i.e., pyruvate) after the storage period by less than 10%, more preferably less than 5%, even more preferably less than 3%, 2% or 1%, more preferably no increase at all, and in one embodiment a reduction in pungency, compared to the measurement at harvest (or shortly after harvest). "No significant reduction in SSC" refers herein to a reduction in SSC levels after the storage period of less than 5%, 4%, 3% or 2%, preferably less than 1% or 0.5%, more preferably unchanged, compared to the SSC level at harvest (or shortly after harvest). In one embodiment the mean SSC level after 2, 3, 4, 5, 6, 7 or more months of storage is at least about 80%, 85%, 87%, 88%, 89%, 90%, 95%, 98% of the level at harvest, more preferably at least about 100%, or 101%, 102%, 103%, 105% of the level at harvest, or more.

An onion plant (and seed of an onion plant, and parts derived from such a plant) requiring 14 or more contiguous hours of daylight to initiate bulb formation is provided, whereby the bulb has a low pungency, especially at harvest and also after a certain period of storage. Preferably the bulb also has a high soluble solid content (SSC), especially at harvest and after a certain period of storage. The bulb substantially maintains low pungency after storage for about 2, 3, 4, 5, 6, 7 or more months. Preferably pungency levels decrease during storage. The bulb also substantially maintains high SSC content for about 2, 3, 4, 5, 6, 7 or more months.

In one aspect, the invention provides onion plants, bulbs and seeds, whereby the bulbs comprise a low (mean) pungency at harvest, a high (mean) SSC and/or a long storage ability. The (mean) pungency at harvest is preferably less than 5.5, 5.0, 4.5, 4.0 $\mu$Mol/g FW, or even equal to or less than 3.8 or 3.75 $\mu$Mol/g FW, or equal to or less than 3.5, 3.0, 2.5, 2.3, 2.0, 1.8, 1.5, 1.3 $\mu$Mol/g FW or less. The (mean) SSC at harvest and/or after storage (for 2, 3, 4, 5, 6, 7, 8 or more months) is preferably at least 7.0%, 7.2%, 7.5% or even at least 8%, 9%, 10%, 11%, 12%, 15%, 20%, 25%, 30% or more. The bulbs according to the invention can be stored for at least 2, 3, 4, 5, 6, 7 or more months, preferably without any significant increase in pungency at the end of storage and/or without any significant reduction in SSC. The mean pungency measured after 2, 3, 4, 5, 6, 7 or more months of storage is preferably equal or less than 5.5, 5.0, 4.5, 4.0 $\mu$Mol/g FW or even equal to or less than 3.8 or 3.75 $\mu$Mol/g FW, equal to or less than 3.5, 3.0, 2.5, 2.3, 2.0, 1.8, 1.5, 1.3 $\mu$Mol/g FW or less. In one aspect, the mean pungency (PAD measurement) after a certain period of storage is lower than at harvest, i.e. pungency levels decrease during storage. The (mean) SSC after 2, 3, 4, 5, 6, 7 or more months of storage is preferably at least 7.0%, 7.2%, 7.5%, or even at least 8%, 9%, 10%, 11%, 12%, 15%, 20%, 25%, 30% or more.

In addition, the onion plants provided herein produce bulbs which have a narrow pungency range as defined above. This characteristic is an important feature for the consumer of fresh onions, as often a bag of onions are bought but individual onions are used for the preparation of food. Thus, in one embodiment a plurality of (harvested and optionally stored and/or packaged) onion bulbs are provided which have a narrow pungency range, as are plants which are capable of producing such bulbs. In particular, the maximum pungency level of a bulb produced by a plant according to the invention (measured at harvest or after 2, 3, 4, 4.5, 5, 6, 7 or more months of storage) is equal to or less than 5 µMol/g FW, preferably equal to or less than 4.9, 4.8, 4.7, 4.5, 4.0 or 3.8, 3.75, 3.5 or 3.0 µMol/g FW. Thus, a plant according to the invention produces onion bulbs having PAD measurements within the ranges of about 1.0-5.0 (min-max), 1.0-4.9 (min-max), 1.0-4.8, 1.0-4.7, 1.0-4.0 or 1.0-3.8, 1.0-3.5, 1.0-3.0 µMol/g FW. Consumers who buy bulbs of a plant according to the invention will therefore have onions of similar pungency, as the pungency range (i.e. the variation in bulb-pungency within a plant according to the invention) is narrow. The onions are, therefore, all mild (non-pungent or sweet) onions.

Also progeny of the above plants are provided (obtained by selfing or crossing), which retain bulbs with a low level of pungency, high SSC content and/or long storage ability. i.e. which are substantially identical to the bulbs of the parent(s) for these traits. Progeny include thus, for example inbred plants producing bulbs with one or more of the above traits or hybrid plants producing bulbs with one or more of the above traits.

Also parts of the above onion plants are provided. Such plant parts, derived from the onion plants described herein, may be a seed, a bulb, a leaf, a flower, pollen, stamen, an ovule, a cell, a protoplast, a tissue culture of cells or the like. A tissue culture of cells may, for example, be derived from a tissue selected from a leaf, pollen, embryo, bulb, flower, anther, pollen, ovule, bud, meristem or any cell.

In one aspect, the invention relates to long-day onion seeds deposited by Nunhems B.V. at the American Type Culture Collection (ATCC, 10801 University Boulevard, Manassas, Va. 20110-2209, USA) under the Budapest Treaty under ATCC Accession Numbers PTA-9053 (seeds of line I37853B), PTA-9054 (seeds of line I37554A) and PTA-9055 (seeds of line I37554B) on Mar. 13, 2008, or any derivatives thereof, such as progeny obtained by selfing any one of the deposited plants or by crossing of any one of the deposited plants with another onion plant. In one aspect, derivatives include inbred onion plants which comprise the low pungency, high SSC and/or long storage ability as described. In another aspect, derivatives include onion plants or seeds (and bulbs) obtained from using one or more of these lines (I37554A or B, I37853 or a derivative of any of these) as a parent in one or more crosses with a further onion plant and/or one or more selfings, whereby the progeny have the same (or better) low pungency, high soluble solid phenotypes and/or storage properties as defined above and/or as the deposited lines. Therefore, derivatives may include hybrid onion plants or seeds (and bulbs of such plants) which produce/are capable of producing bulbs having the above (or better) low pungency, high SSC and/or long term storage abilities as described above and/or as the bulbs of I37853 and/or I37554A or B. Derivatives of the hybrids are also encompassed herein. In another aspect, hybrid seeds, plants and bulbs obtainable from crossing I37853 (or a derivative thereof, such as an inbred) with another onion plant, e.g. with I37554A or B (or a derivative thereof, such as an inbred) are provided, as well as plants, bulbs and seeds obtained from using such F1 hybrids in further selfings or crosses. Therefore, various long day onion plants having low pungency, high SSC and/or long term storage ability are encompassed herein, including, for example, plants comprising the physiological and morphological characteristics of I37853 and/or I37554A or B. Plants derived, or derivable, from plants according to the invention (e.g. from deposited seeds) include, therefore, plants obtained by breeding methods, such as selfing, crossing, backcrossing, recurrent selection, double haploid production, marker assisted selection, clonal propagations, transformants, etc., whereby the derived plants produce bulbs with low pungency, high SSC and/or long term storage properties as described herein.

Thus, a long day onion plant derived from, or derivable from, one of the plants deposited under ATCC Accession Numbers PTA-9053, PTA-9054 or PTA-9055 by selfing, crossing, clonal propagation, or tissue culture is provided herein, wherein the plant produces onion bulbs having the same (or better) low pungency, high soluble solid phenotypes and/or storage properties (at harvest and/or after storage) as described herein and/or as the deposited lines PTA-9053, PTA-9054 or PTA-9055.

Progeny of the onion plants deposited under PTA-9053, PTA-9054 and PTA-9055 are provided, wherein said progeny produces onion bulbs having the same (or better) low pungency, high soluble solid phenotypes and/or storage properties (at harvest and/or after storage) as described herein and/or as the deposited lines PTA-9053, PTA-9054 or PTA-9055. In one embodiment F1 hybrid plants, as well as seeds from which F1 hybrid plants can be grown, and bulbs produced by these hybrid plants, are provided, whereby at least one inbred onion plant according to the invention is used as one of the parents, preferably selected from I37853, I37554A and I37554B, or derivatives thereof.

Derivatives also include plants obtained from tissue culture methods and tissue cultures themselves, whereby tissue of any of the herein described plants is used (e.g. leaf, pollen, flowers, embryos, protoplasts, etc.). Likewise, transgenic onions of any of the above plants are encompassed herein. Thus, onion plants into which one or more genetic elements have been introduced by transformation are also encompassed herein. Transformation and regeneration of onion uses methods known in the art. For example, one or more genes for herbicide resistance or resistance against microorganisms may be introduced. Likewise, transgenes may be introduced into the onions according to the invention by crossing the onion plant with a plant comprising the transgene(s) and selecting offspring comprising the transgene(s).

Preferably there is no significant increase in pungency and/or no significant reduction in SSC during the storage period of the bulbs, i.e., when comparing the average pungency and/or average SSC at harvest (or shortly after harvest) with the average pungency and/or average SSC level after 2, 3, 4, 5, 6, 7 or more months of storage. "No significant increase in pungency" refers herein to an increase in pungency measurement (i.e., pyruvate) after the storage period by less than 10%, preferably less than 5%, more preferably less than 3%, 2% or 1%, more preferably no increase at all, and optionally even a reduction in pungency, compared to the measurement at harvest (or shortly after harvest). A reduction in pungency compared to pungency at harvest includes, for example, a reduction by at least 0.5%, 1% or more. Thus, when average pungency at harvest is compared to average pungency after 2, 3, 4, 5, 6, 7, and/or 8 months of storage, average PAD measurements after storage is lower than at harvest, i.e. equal to or less than 99.5%, 99%, 98%, 97%, 96%, 95%, 94%, 93%, 90%, 85%, 80%, 70% of the level at harvest. "No significant reduction in SSC" refers herein to a reduction in SSC levels after the storage period of less than 2%, preferably less than 1% or 0.5%, more preferably unchanged, compared to the SSC level at harvest (or shortly after harvest).

Also the pungency range preferably remains narrow during storage, so that the pungency range is narrow at harvest and/or after 2, 3, 4, or more months of storage as described. Equally, the maximum pungency of the bulbs (the most pungent bulb) produced by the plant is in one embodiment equal to or lower than at harvest. In addition, decay after at least 2, 3, 4, 5, 6, 7 or more months of storage (as can be measured visually and/or by weight, e.g., weighing non-decayed bulbs and comparing their weight to the total weight at the beginning of storage), is low, i.e., at any given time-point, e.g., after about 2, 2.5, 3, 3.5, 4, 4.5, 5, 5.5 or 6 months of storage or more, decay is less than 10%, preferably less than 9%, 8%, 7.2%, 7%, 6%, 5%, 4%, 3%, 2%, 1% or even less. Therefore, the percentage of marketable bulbs (no decay) remains high during storage, after at least about 4.5 months of storage at least 90%, 91%, 92% or more is not decayed. In one embodiment after 5 months of storage, at least about 83%, 84%, 85%, 86%, 87%, 88% 89%, 90%, 91%, 92%, 93%, 94%, 95% or more of the bulbs are non-decayed. In one embodiment after 6 months of storage, at least about 76%, 77%, 78%, 79%, 80%, 81%, 82%, 83%, 84%, 85%, 86%, 87%, 88% 89%, 90%, 91%, 92%, 93%, 94%, 95% or more of the bulbs are non-decayed The onion plants, bulbs and seeds are long-day onions, i.e., the plants initiate bulb formation under long periods of contiguous light, e.g. artificial or natural light of at least about 14 hours or more. The onion plant thus preferably requires 14 or more hours per day (per 24 hours) of contiguous light in order to initiate bulb formation.

In one aspect, the onion plants, or seeds provided herein are capable of forming bulbs which have a pungency of less than 3.75/g FW, preferably equal to or less than 3.5, 3.0, 2.5, 2.3, 2.0, 1.8, 1.5, 1.3 µMol/g FW when measured 2, 3, 4, 5, 6 or 7 months after harvest, e.g. after 5-6 months of storage in the dark, under cool temperatures and at a RH of 60-80%. These bulbs have a significantly lower average pungency than bulbs of seeds deposited under NCIMB Accession Numbers 41329 and 41330 (described in WO2007/011857), as well as preferably a narrower pungency range than various onion lines described in WO2007/011857. Also the pungency (PAD measurement) of the most pungent bulb obtained from a plant according to the invention is lower than that of the most pungent bulb produced by NCIMB 41329 and 41330. In addition, the bulbs have at least an equivalent, preferably a significantly higher average SSC content than bulbs of seeds deposited under NCIMB Accession Numbers 41329 and 41330 and/or a longer storage ability (less storage decay) compared to such bulbs. When comparing plants or bulbs according to the invention with other plants it is understood that one should use the same environmental conditions and same measurement methods. Appropriate control plants can also be included, such as varieties Granero or Nebula or others. Plants can be grown on any soil and with standard fertilization, although in soil specifically managed for low sulphur, or soil naturally low in sulphur, PAD measurements will be even lower than described herein.

It was found that bulbs and plants having very low pungency and high SSC content can be selected for, which was believed to be impossible. Without limiting the invention, it is thought that the genetic linkage between one or more regions responsible for high pungency and regions responsible for high SSC can, contrary to prior belief, be broken, enabling the selection or identification of low pungency/high SSC plants. Plants provided herein can be made as described in the methods and Examples herein below, using breeding and selection methods (PAD measurements, SSC measurements and/or storage decay measurements and the like). Also seeds provided herein can be used to make plants according to the invention, as the traits can be transferred from the deposited seeds to other onion plants by crossing and selection. Basically the traits (low pungency, high SSC and/or long storage ability) can be introduced into any long day onion, such as for example Spanish onions, Spanish-type onions, (northern) yellow-type onions, white and red type onions, hard-globe eastern or western type onions, etc. Onion plants (e.g., open pollinated or hybrid plants) can therefore be made having these traits and having good agronomic characteristics, such as disease resistance (e.g. Fusarium resistance, *Peronospora destructor* resistance as e.g. described in WO2006061256, pink root resistance, *Botrytis* resistance, Purple Blotch resistance, *Stemphylium* resistance, bacterial streak and bulb rot resistance, center rot resistance, *Erwinia* resistance, virus resistance, etc.) bulb size, % single centers, bolting tolerance, etc.

Also provided herein are containers comprising a plurality of onion bulbs having the above phenotypes, as well as containers comprising a plurality of onion seeds of the above plants or containers comprising a plurality of onion plants or seedlings. Containers may be of any type, such as bags, cans, tins, trays, boxes, flats and the like. Also provided herein are containers comprising onion bulbs having an average PAD measurement of less than about 5.5 µMol/g FW, preferably less than 3.75, 3.5, 3.0, etc. µMol/g FW, high SSC and/or long storage ability (each phenotype as defined above). Preferably in a container at least 75%, 85%, 95%, 98% or more of the bulbs have such a PAD measurement, SSC level and/or storage ability. Also, preferably the pungency range of all bulbs in a container is narrow, as described. The most pungent bulb preferably has a pungency of equal to or less than 5.5, 5.0, 4.8, 4.7, 4.5, 4.0, 3.5, or less at harvest or after storage. A container preferably contains at least about 1 pound, 5 pounds, 10 pounds or more bulbs. The container may be in any location, e.g., a store (such as a grocery store), warehouse, market place, distributor, etc.

Seed containers comprising seeds of an onion plant requiring 14 or more hours contiguous light to initiate bulb formation, wherein the seed is capable of producing an onion plant having a bulb comprising low pungency (i.e., a PAD measurement as defined), high SSC and/or long storage ability (also as defined) are also provided. Preferably the onion bulbs from greater than 50%, more preferably from greater than 60%, 70%, 75%, 80%, 90%, 95%, 98% of the plants produced by such seeds produce bulbs having an average PAD measurement of less than 5.5 µMol/g FW, preferably less than 5.0, 4.0, 3.5, or 3.0 µMol/g FW, etc., high SSC and/or long storage ability. The containers preferably comprise at least 100, 500, 1000, 10.000 or more seeds and is preferably selected from a bag, box, packet, tin or can. Also, preferably the pungency range of all bulbs derivable from the seeds in a container is narrow. In one embodiment the maximum pungency of a bulb produced from the seeds has a pungency of equal to or less than 5.5, 5.0, 4.8, 4.7, 4.5, 4.0, 3.5, or less at harvest or after storage.

In another aspect, a method for producing an onion plant or seed, or a group of plants or seeds, is provided, whereby the plant, or group of plants, produce(s) a bulb after exposure to at least about 14 hours light per day (during a period of at least about 1 or more weeks, e.g., 2 or 3 or more weeks) which comprises a (single bulb or mean) pungency of less than 5.5, 5.0, 4.0, 3.75 µMol/g FW at harvest (or less, as defined above) and a (single bulb or mean) SSC at harvest of at least 7.0% or more or 7.5% or more (as defined above). Preferably, the bulbs retain low pungency and high SSC during storage. Thus, in one aspect plants are provided which produce bulbs having a mean pungency after 2, 3, 4, 5, 6, 7 or more months of storage of equal to or less than 5.5, 5.0, 4.5, 4.0 µMol/g FW or even equal to or less than 3.8 or 3.75 µMol/g FW, preferably equal to or less than 3.5, 3.0, 2.5, 2.3, 2.0, 1.8, 1.5, 1.3 µMol/g FW or less and a (mean) SSC of at least 7.0%, 7.2%, 7.5% or even at least 8%, 9%, 10%, 11%, 12%, 15%, 20%, 25%, 30% or more. Also, the pungency range of the bulbs is preferably narrow and the PAD measurement of the most pungent bulb is below 6.0, preferably equal to or less than 5.5, 5.0, 4.0, 3.5 or less. The method comprises crossing two parent onion plants or selfing an onion plant and harvesting the resulting onion seeds from the cross or selfing, wherein at least one parent is an onion plant as described above, or a derivative thereof. Seeds produced by the method are also provided herein, as are onion plants produced by growing those seeds and onion bulbs harvested from those grown plants.

The method may further comprise the step of growing an F1 hybrid onion plant obtained from seed obtained from said cross, crossing the F1 onion plant to another onion plant, e.g., to one of the parents used, and selecting progeny onion plants having the desired low pungency and high SSC content.

In a further aspect, a method for producing an onion plant or seed or a group of onion plants or seeds, is provided, whereby the plant, or group of plants, produce(s) (a) bulb(s) after exposure to at least about 14 hours light per day (during a period of at least about 1 or more weeks, e.g., 2 or 3 or more weeks) which comprises a (single bulb or mean) pungency of less than 5.5, 5.0, 4.0, 3.75 µMol/g FW at harvest (or less, as defined above) and a (single bulb or mean) SSC at harvest of at least 7.0, 7.2 or 7.5% or more (as defined above). Preferably, the bulbs retain low pungency and high SSC during storage, show little decay during storage and/or have a narrow pungency range (all as described). The method comprises the steps of:
 a) crossing an onion plant producing bulbs having a low SSC and low pungency with an onion plant producing bulbs having a high SSC and high pungency,
 b) obtaining the F1 seeds from said cross,
 c) selfing and/or crossing the plants obtained from the F1 seeds one or more times with one another or with other onion plants, and
 d) identifying and selecting progeny plants which produce bulbs having a low pungency and high SSC by phenotyping the bulbs.

Optionally steps c) and/or d) can be repeated several times. Crossing in step c) may also involve backcrossing. In step d), plants having a narrow pungency range and/or plants showing little decay during storage may be selected. Thus, pungency range and/or storage ability can also be used as selection criteria in addition to or as an alternative of low pungency and/or high SSC. The same applies to the methods described herein below, even if only SSC and pungency are mentioned.

The phenotyping preferably involves determining the pungency, SSC content and/or storage ability (e.g. percentage decay after a certain storage period, which can be analysed visually) of the bulbs (e.g. by phenotyping one or more populations of step c) above) and selecting rare recombinants or mutants which have a low pungency and/or high SSC and/or long storage ability. The plants used under a) may be commercially available onion cultivars or breeding lines, such as long day onions and short day onions. Phenotyping can be carried out on a plurality of single bulbs independently, preferably grown under the same conditions next to suitable controls, or on a sample composed of (all or parts of) several bulbs. When single bulbs are used, preferably the mean value is calculated from a representative number of bulbs. Phenotyping can be done one or more times. For example PAD measurements and/or SSC measurements may be carried out at harvest and after 1, 2, 3, 4 or more weeks of storage or 2, 3, 4, 5, 6, 7, 8, 9 or more months of storage. In one embodiment the phenotyping (PAD and/or SSC measurements) is carried out after about 5, 6 or 7 months of storage (e.g. after about 150-210 days, e.g. about 150 days, 180 days, 200 days or 205, 206, 207, 208, 209, 210 days of storage). Phenotyping can be carried out at one or more steps of a breeding scheme.

Phenotyping may also comprise an analysis of the photoperiod response and selection of plants having a long-day response, so that in step d) long day onions are produced.

In one aspect a method for making long-day onion plants comprising a low pungency and high SSC, is provided, comprising a) (optionally) analyzing onion bulbs for pungency and SSC, b) crossing plants producing bulbs having a high pungency and high SSC with plants producing bulbs with a low pungency and low SSC to produce F1 hybrids, c) selfing and/or (back)crossing F1 hybrid plants one or more times and d) selecting progeny plants for low pungency and high SSC content (at harvest and/or after storage) and preferably also for having a long day length photoperiod response and/or preferably also for having a narrow pungency range and e) selecting a long day onion plant producing bulbs having low pungency and high SSC, with levels similar to those of lines PTA-9053, PTA-9054 or PTA-9055 at harvest and/or after storage. Step d) involves pungency and SSC analysis at harvest and/or after storage. In the initial cross, the low pungency, low SSC onion parent may be a short-day onion variety, cultivar or breeding line and the high pungency, high SSC may be a long day onion variety, cultivar or breeding line. Preferably steps c) and d) are repeated several times, so that several cycles of phenotypic recurrent selection are carried out, leading to long day onions of step e).

In yet a further aspect, a method of producing an inbred, long-day onion plant comprising low pungency and high SSC is provided herein, comprising the steps of:
 a) the creation of variable populations of *Allium cepa* comprising the steps of crossing a plant or plants producing bulbs with low pungency and high SSC (as described herein) with a plant of the species *Allium cepa*,
 b) harvesting the F1 seed from any of the plants used in the cross of a) and growing F1 plants from the seed harvested,
 c) selfing the plants grown under b) or crossing these plants amongst one another, or crossing these plants with plants of *Allium cepa*,
 d) growing plants from the resulting seed harvested under normal plant growing conditions and,
 e) selecting plants producing bulbs having low pungency and high SSC, followed by selfing the selected plants, and optionally
 f) repeating the steps d) and/or e) until the inbred lines are obtained which are homozygous and can be used as parents in the production of hybrids having low pungency and high SSC.

Also provided is a method for developing male sterile inbred lines with the properties of low pungency and high SSC comprising the steps of crossing the plants of the inbred lines described above with plants of male sterile lines of *Allium cepa* and the subsequent selection and recurrent back crossing with the male fertile parent until the new male sterile line is genetically and phenotypically similar to the male fertile recurrent parent inbred line and has the combination of low pungency and high SSC. Thus, a male sterile inbred line producing bulbs having low pungency, high SSC and/or low storage decay is also an embodiment of the invention.

The male sterile inbred line may be crossed with a male fertile inbred line resulting in hybrid seeds, whereby the plants grown therefrom possess the properties of low pungency and high SSC.

Likewise open pollinated, long-day onion plants comprising low pungency and high SSC can be made. Thus, onion plants according to the invention may be maintained as open pollinated lines, half-sib lines, male sterile lines, female sterile lines, etc. Male sterile inbred lines of onion plants according to the invention are useful as parents for producing hybrids.

In another aspect, a method for producing an onion crop from onion seeds or plants according to the invention and long day onions harvested therefrom is provided. Also processed bulbs or bulb parts are encompassed herein, such as sliced or diced bulbs, dried bulbs or parts thereof and food or feed products comprising or consisting of bulbs or bulb parts according to the invention, such as fresh salads, sandwiches, etc. To produce an onion crop, herbicides, fungicides and/or insecticides may be applied, such as the following non-limiting products: (Herbicides) Atrazine, Bromacil, Diuron, Glyphosate, Linuron, Metribuzin, Simazine, Trifluralin, Fluazifop, Glufosinate, Halosulfuron Gowan, Paraquat, Propyzamide, Sethoxydim, Butafenacil, Halosulfuron, Indaziflam; (Insecticides) Aldicarb, Bacillus thuriengiensis, Carbaryl, Carbofuran, Chlorpyrifos, Cypermethrin, Deltamethrin, Abamectin, Cyfluthrin/beta-cyfluthrin, Esfenvalerate, Lambda-cyhalothrin, Acequinocyl, Bifenazate, Methoxyfenozide, Novaluron, Chromafenozide, Thiacloprid, Dinotefuran, Fluacrypyrim, Spirodiclofen, Gamma-cyhalothrin, Spiromesifen, Spinosad, Rynaxypyr, Cyazypyr, Triflumuron, Spirotetramat, Imidacloprid, Flubendiamide, Thiodicarb, Metaflumizone, Sulfoxaflor, Cyflumetofen, Cyanopyrafen, Clothianidin, Thiamethoxam, Spinotoram, Thiodicarb, Flonicamid, Methiocarb, Emamectin-benzoate, Indoxacarb, Fenamiphos, Pyriproxifen, Fenbutatin-oxid; (Fungicides) Ametoctradin, Azoxystrobin, Benthiavalicarb, Boscalid, Captan, Carbendazim, Chlorothalonil, Copper, Cyazofamid, Cyflufenamid, Cymoxanil, Cyproconazole, Cyprodinil, Difenoconazole, Dimetomorph, Dithianon, Fenamidone, Fenhexamid, Fluazinam, Fludioxonil, Fluopicolide, Fluopyram, Fluoxastrobin, Fluxapyroxad, Folpet, Fosetyl, Iprodione, Iprovalicarb, Isopyrazam, Kresoxim-methyl, Mancozeb, Mandipropamid, Metalaxyl/mefenoxam, Metiram, Metrafenone, Myclobutanil, Penconazole, Penthiopyrad, Picoxystrobin, Propamocarb, Propiconazole, Propineb, Proquinazid, Prothioconazole, Pyraclostrobin, Pyrimethanil, Quinoxyfen, Spiroxamine, Sulphur, Tebuconazole, Thiophanate-methyl, Trifloxystrobin, The taste of onion bulbs in accordance with the present invention can be determined by a trained sensory panel. For example, such a trained sensory panel may consist of at least 4, 5, 6, or more trained subjects. Each subject should determine the taste of at least 3, 4, 5 or more onion bulbs per variety/line. For example, this test is suitable to determine the flavor of onion bulbs such as the sweet taste balance. The acceptance score can be rated on a 1-15 scale with the following categories:

| | |
|---|---|
| 1-3 | unacceptable |
| 4-6 | below average |
| 7-9 | average |
| 10-12 | good |
| 13-15 | excellent |

In one embodiment, an onion bulb of the present invention has an acceptance score of at least 10.5, at least 10.8, at least 11.0 or at least 11.5 after 4, 5, 6, 7 or more months after harvest.

The following non-limiting examples illustrate the production of onion plants, seeds and bulbs according to the invention. All references mentioned herein are incorporated by reference.

EXAMPLES

Example 1

Plant Development

Plants have been obtained by a long term breeding program (Oregon, USA) in which numerous plants have been analyzed for the desired combination of the traits as mentioned.

The initial cross concerned low pungency/low SSC onion plants (the commercially available long-day variety Ailsa Craig) with high pungency/high SSC long-day onion plants of a breeding line designated I37787B and subsequent selfing of the F1 plants to create variable F2 populations. No Spanish background was used.

A selected F2 individual (phenotyped for pungency and SSC) was crossed to an individual selected from a breeding line derived from the variety Oregon Danvers Yellow Globe. Plants from this cross where selfed and selected individuals from this progeny were selfed again. A low pungency, high SSC line was obtained and designated I37554.

Six additional cycles of phenotypic recurrent selection were made, with selection for the phenotypes high SSC and low pungency and having all desirable agronomic traits and long day length photoperiod response. High SSC was determined using refractometry analysis according to the method of Mann and Hoyle, 1945 (Proc. Americ. Soc. Hort. Sci. 46: 285-292) or Foskett and Peterson, 1949 (Proc. Americ. Soc. Hort. Sci. 55: 314-318). Pungency was determined using the PAD measurement of Schwimmer and Weston 1961 (supra). Throughout the scheme plants in each generation were selected after approximately 150 days of storage, i.e., PAD and/or SSC measurements were made after about 5 to 6 months of storage for selection purposes.

Coincident with the six cycles of phenotypic recurrent selection the selected plants were crossed and backcrossed to cytoplasmic/nuclear male sterile plants. In this way inbred maintainer line I37554B and its male sterile companion line I37554A were developed, both of which have lower pungency and higher SSC at harvest and after storage and are long day onions. Seeds of I37554 (I37554A and I37554B) have been deposited at the ATCC under the Budapest Treaty under ATCC Accession Numbers PTA-9054 and PTA-9055, respectively.

Line I37853B was developed by further breeding and selection with the above material and seeds of I37853B were deposited at the ATCC under the Budapest Treaty under ATCC Accession Number PTA-9053. Line I37853B has even lower pungency than I37554A and B and has improved bulb quality.

From these plants parent lines for producing hybrid varieties have been developed by additional crossing and further inbreeding while selecting for agronomic traits and good combining ability. The hybrid varieties produced with these lines have been evaluated for the unique combination of low pungency/high soluble solids, long storage and other desirable agronomic characteristics.

In one aspect of the invention, novel plants, seeds and bulbs of long-day onion I37554A or B and of I37853B are provided. Also, hybrids produced from crossing I37554A or B and I37853B are provided, as well as plants produced from such crosses or selfings and which produce bulbs comprising low pungency, high SSC and/or high storage capabilities.

Example 2

Plant I37554 Having Low Pungency and High SSC

Table 1 below shows (average) pungency measured as pyruvate concentration in μMol/g FW and SSC content (%) of bulbs of the plant designated I37554A and the commercially available Long Day variety Granero 9536, both at harvest and during 3 months of storage.

TABLE 1

| Time Period* | Pyruvate (μMol/g FW) Granero | I37554 | SSC (%) Granero | I37554 |
|---|---|---|---|---|
| 1 | 6.22 | 4.92 | 8.6 | 8.3 |
| 2 | 5.95 | 5.34 | 9.3 | 8.5 |
| 3 | 5.91 | 5.5 | 9.7 | 8.9 |
| 4 | 6.92 | 6.17 | 8.3 | 8.1 |
| 5 | 8.66 | 5.78 | 9.4 | 8.1 |
| 6 | 9.07 | 3.33 | 8.4 | 8.2 |
| 7 | 8.53 | 4.89 | 8.1 | 7.5 |
| 8 | 9.97 | 4.62 | 8.5 | 7.4 |

*The time periods are approximately two weeks apart.

The Example shows that during storage pyruvate levels of Granero, a long day Spanish hybrid variety which is pungent and has high SSC, increases significantly, while the pungency of I37554A does not change significantly and the SSC levels remain high and constant. Also, at harvest I37554A, combines low pungency with high SSC (and long day characteristics).

Example 3

Table 2 shows yield and percent storage decay of I37554A compared to commercial pungent and high SSC varieties Granero and Nebula (136 days after harvest, i.e., after about 4.5 months of storage). Percent decay was assessed by weight.

TABLE 2

| Plant | Yield (lbs/acre - 100's) Total | Large | Medium | Small | Weight/bulb (g) | Storage decay Decay (%) | No decay (%) |
|---|---|---|---|---|---|---|---|
| I37554A | 595 | 401 | 134 | 14.5 | 179.5 | 7.1 | 92.9 |
| Granero | 680 | 539 | 104 | 3.5 | 225.0 | 5.5 | 94.5 |
| Nebula | 380 | 169 | 182 | 11.4 | 142.7 | 3.4 | 96.6 |

The Example shows that, while having low pungency, line I37554A has similar, good storage characteristics as known pungent storage onions which have high SSC.

Example 4

Table 3 shows pungency and SSC data for I37554B after more than 6 months (207 days, i.e., 6.9 months) of storage. Table 3 shows data for 92 single bulbs of I37554B and the mean.

TABLE 3

| Plot number | Pungency (μMol/g FW) | SSC (%) |
|---|---|---|
| 6111 | 2.52 | 9.20 |
| 6111 | 4.15 | 10.20 |
| 6111 | 2.70 | 9.20 |
| 6111 | 3.63 | 9.20 |
| 6111 | 2.62 | 9.80 |
| 6111 | 3.22 | 8.80 |
| 6111 | 4.37 | 8.80 |
| 6111 | 2.41 | 10.20 |
| 6111 | 3.56 | 10.20 |
| 6111 | 3.57 | 8.20 |
| 6111 | 3.03 | 7.80 |
| 6111 | 4.50 | 10.20 |
| 6111 | 3.88 | 10.20 |
| 6111 | 2.77 | 7.60 |
| 6111 | 3.48 | 9.20 |
| 6111 | 3.42 | 9.00 |
| 6111 | 3.54 | 10.40 |
| 6111 | 2.82 | 9.20 |
| 6111 | 4.41 | 10.80 |
| 6111 | 1.90 | 9.40 |
| 6111 | 2.86 | 9.80 |
| 6111 | 2.67 | 9.40 |
| 6111 | 3.29 | 9.80 |
| 6111 | 2.69 | 8.80 |
| 6111 | 4.03 | 9.00 |
| 6111 | 2.86 | 8.80 |
| 6111 | 2.76 | 8.80 |
| 6111 | 3.04 | 8.40 |
| 6111 | 3.50 | 9.40 |
| 6111 | 4.29 | 9.40 |
| 6111 | 4.13 | 7.80 |
| 6111 | 3.25 | 8.60 |
| 6111 | 2.05 | 9.80 |
| 6111 | 3.93 | 10.20 |
| 6111 | 3.42 | 9.80 |
| 6111 | 3.56 | 10.40 |
| 6111 | 3.15 | 8.20 |
| 6111 | 3.59 | 10.20 |
| 6111 | 2.86 | 10.20 |
| 6111 | 3.16 | 10.20 |
| 6111 | 2.36 | 8.60 |
| 6111 | 4.15 | 10.80 |
| 6111 | 3.20 | 9.00 |
| 6111 | 2.49 | 9.40 |
| 6111 | 3.35 | 10.80 |
| 6111 | 4.47 | 10.60 |
| 6111 | 3.87 | 9.80 |
| 6111 | 3.87 | 9.60 |
| 6111 | 4.17 | 10.40 |
| 6111 | 2.59 | 9.80 |
| 6111 | 1.29 | 10.20 |
| 6111 | 4.08 | 9.60 |
| 6111 | 3.25 | 8.80 |
| 6111 | 2.43 | 8.60 |
| 6111 | 3.10 | 9.40 |
| 6111 | 4.54 | 8.20 |
| 6111 | 4.12 | 9.80 |
| 6111 | 3.57 | 10.40 |
| 6111 | 3.62 | 10.40 |
| 6111 | 3.09 | 8.40 |
| 6111 | 2.92 | 9.00 |
| 6111 | 4.44 | 10.20 |
| 6111 | 1.76 | 9.80 |
| 6111 | 4.39 | 9.80 |
| 6111 | 3.23 | 10.40 |
| 6111 | 3.69 | 10.20 |
| 6111 | 4.20 | 11.20 |
| 6111 | 4.35 | 9.40 |
| 6111 | 4.29 | 10.40 |
| 6111 | 4.14 | 10.20 |
| 6111 | 4.43 | 10.20 |
| 6111 | 3.97 | 10.20 |
| 6111 | 3.72 | 10.40 |
| 6111 | 3.53 | 10.40 |
| 6111 | 4.17 | 11.60 |
| 6111 | 3.67 | 10.20 |
| 6111 | 4.30 | 10.00 |

TABLE 3-continued

| Plot number | Pungency (µMol/g FW) | SSC (%) |
|---|---|---|
| 6111 | 3.41 | 9.40 |
| 6111 | 4.17 | 9.80 |
| 6111 | 2.85 | 9.00 |
| 6111 | 4.74 | 9.80 |
| 6111 | 3.14 | 9.80 |
| 6111 | 4.17 | 10.00 |
| 6111 | 3.80 | 11.20 |
| 6111 | 3.83 | 10.20 |
| 6111 | 3.75 | 10.20 |
| 6111 | 2.84 | 9.80 |
| 6111 | 4.32 | 9.40 |
| 6111 | 4.63 | 10.40 |
| 6111 | 3.04 | 9.60 |
| 6111 | 3.78 | 10.00 |
| 6111 | 4.84 | 9.80 |
| MEAN | 3.5 | 9.67 |

The data show that line I37554B has low pungency and high SSC levels. Even after more than 6 months of storage the average pungency remains very low and average SSC remains high. Also, the pungency range is narrow (min. 1.29, max. 4.85).

Example 5

Line I37853B

Table 4 shows single bulb pungency levels of line I37853B after 5-6 months of storage showing that very low pungency (mean pungency 2.3 µMol/g FW) has been achieved, combined with high SSC.

TABLE 4

| Pungency (µMol/g FW) |
|---|
| 1.3 |
| 1.4 |
| 3.7 |
| 4.7 |
| 3.3 |
| 2.3 |
| 3.1 |
| 2.1 |
| 3.0 |
| 2.0 |
| 2.6 |
| 2.1 |
| 2.4 |
| 1.6 |
| 2.4 |
| 2.3 |
| 2.2 |
| 3.0 |
| 1.2 |
| 2.6 |
| 1.9 |
| 2.1 |
| 3.6 |
| 2.0 |
| 1.8 |
| 2.0 |
| 3.0 |
| 1.3 |
| 2.1 |
| 1.8 |
| 1.3 |
| 2.4 |
| 2.2 |
| 2.5 |
| 1.9 |

TABLE 4-continued

| Pungency (µMol/g FW) |
|---|
| 2.0 |
| 3.7 |
| 1.9 |
| Mean (38 bulbs) = 2.3 |

Example 6

Hybrids

To generate hybrids of long day storage onions having low pungency and high SSC at harvest and after long term storage, line I37554A (female parent) was crossed with I37853B (male parent) to generate F1 hybrid seeds. The hybrids will be grown at various locations and pyruvate and SSC levels will be assessed and compared to the parents and high pungency lines or cultivars.

Example 7

Line I37554B

Table 5 shows average pungency (pyruvate µMOL/g FW), SSC (%) and Storage Decay (%) of line I37554B after storage (132 days after harvest).

TABLE 5

| Name | Pyruvate (µMol/g FW) | SSC (%) | Storage Decay (%) | No decay (%) |
|---|---|---|---|---|
| I37554B | 3.8 | 8.6 | 9.1 | 90.9 |

Example 8

I37554, SR 5628, SR 5630, SR 5634 and SR 5637
(at Harvest)

Average pungency measured as pyruvate concentration (µMol/g FW) and Percent Soluble Solids (SSC %) of bulbs of several onion lines and varieties. Onions were grown near Boardman, Oreg., harvested Sep. 8, 2010 and tested on Sep. 16 and 17, 2010. SR 5628, SR 5630, SR 5634 and SR 5637 are hybrids from the same germplasm as I37554 (Table 6). Average pungency of harvested onion bulbs of Seminis seed deposits (see WO 2007/011857) measured as pyruvate concentration (µMol/g FW) and Percent Soluble Solids (SSC %) of bulbs which were grown near Brooks, Oreg., harvested Sep. 6, 2010 and tested on Sep. 17, 2010 (Table 7).

TABLE 6

| Name | # of bulbs tested | Pyruvate (µMol/g FW) | SSC % |
|---|---|---|---|
| EverMild (Seminis Hybrid Variety) | 6 | 5.9 | 6.3 |
| I37554B | 6 | 4.6 | 7.8 |
| SR 5628 (Nunhems Hybrid) | 6 | 3.8 | 7.2 |
| SR 5630 (Nunhems Hybrid) | 6 | 4.6 | 9.1 |
| SR 5634 (Nunhems Hybrid) | 6 | 4.4 | 8.5 |
| SR 5637 (Nunhems Hybrid) | 6 | 3.9 | 8.0 |

TABLE 7

| Name | # of bulbs tested | Pyruvate (µMol/g FW) | SSC % |
|---|---|---|---|
| NCIMB 41329 | 2 | 6.6 | 6.5 |
| NCIMB 41330 | 4 | 6.9 | 5.4 |

Example 9

SR 5628, SR 5630, SR 5634 and SR 5637 (After Storage)

The bulbs used for this test were grown in 2010 near Boardman, Wash., harvested Sep. 8, 2010 and stored at Brooks station. They were tested in March, 2011, i.e. after five to six months of storage. The pyruvate content and SSC (Brix) were determined (Table 8).

TABLE 8

| Name | # of bulbs tested | Pyruvate (umol/g fwt) | SSC (%) |
|---|---|---|---|
| SR 5628 | 6 | 2.8 | 7.0 |
| SR 5630 | 6 | 2.6 | 8.4 |
| SR 5634 | 6 | 4.0 | 8.0 |
| SR 5637 | 6 | 3.2 | 7.8 |

Example 10

Sensory Test (After Storage)

A trained sensory panel was commissioned. The bulbs of SR 5628, SR 5630, SR 5634 and SR 5637 used for this test were grown in 2010 near Boardman, Wash., and stored at Brooks station for five to six months. They were tested in March, 2011.

The trained panel consisted of 6 subjects. Five bulbs per line were used for the sensory test. Each panelist had to taste each bulb, so each data point was an average of 6 subjects*5 bulbs/subject=30 data points. The acceptance score was rated on a 1-15 scale with the following categories:

| | |
|---|---|
| 1-3 | unacceptable |
| 4-6 | below average |
| 7-9 | average |
| 10-12 | good |
| 13-15 | excellent |

The sweet balance acceptance, were determined (Table 9).

TABLE 9

| Name | # of bulbs tested | Sweet Balance Acceptance* |
|---|---|---|
| SR 5628 | 6 | 11.5 |
| SR 5630 | 6 | 11.8 |
| SR 5634 | 6 | 12.1 |
| SR 5637 | 6 | 11.7 |
| EverMild | 6 | 8.6 |

DEPOSIT INFORMATION

Applicant(s) have made a deposit of at least 2500 seeds of lines 137853B (PTA-9053), 137554A (PTA-9054) and line 137554B (PTA-9055) on Mar. 13, 2008, with the American Type Culture Collection (ATCC), Manassas, Va. 20110 USA. Seeds of SR 5628, SR 5630, SR 5634 and SR 5637 were deposited under the terms of the Budapest Treaty on Oct. 10, 2013, with the NCIMB, Ltd., Bucksburn, Aberdeen, AB21 9YA, Scotland, United Kingdom and given the accession numbers NCIMB 42167, NCIMB 42168, NCIMB 42169, and NCIMB 42170, respectively. Access to the deposits will be available during the pendency of this application to persons determined by the Director of the U.S. Patent Office to be entitled thereto upon request. Subject to 37 C.F.R. §1.808(b), all restrictions imposed by the depositor on the availability to the public of the deposited material will be irrevocably removed upon the granting of the patent. The deposits will be maintained for a period of 30 years, or 5 years after the most recent request, or for the enforceable life of the patent whichever is longer, and will be replaced if it ever becomes nonviable during that period. Applicant does not waive any rights granted under this patent on this application or under the Plant Variety Protection Act (7 USC 2321 et seq.).

The invention claimed is:

1. An onion plant of variety SR 5628 or a seed, bulb, or plant part of said variety, representative seed of said variety having been deposited under NCIMB Accession No. 42167.

2. The plant part of claim 1, wherein said plant part is a cell, protoplast, an ovule, a meristem, an embryo, or a plant organ.

3. A tissue culture of cells obtained from the plant of claim 1, wherein said tissue culture of cells is from a tissue from the leaf, pollen, embryo, bulb, anther, flower, bud, or meristem.

4. An onion plant of variety SR 5630 or a seed, bulb, or plant part of said variety, representative seed of said variety having been deposited under NCIMB Accession No. 42168.

5. The plant part of claim 4, wherein said plant part is a cell, protoplast, an ovule, a meristem, an embryo, or a plant organ.

6. A tissue culture of cells obtained from the plant of claim 4, wherein said tissue culture of cells is from a tissue from the leaf, pollen, embryo, bulb, anther, flower, bud, or meristem.

7. An onion plant of variety SR 5634 or a seed, bulb, or plant part of said variety, representative seed of said variety having been deposited under NCIMB Accession No. 42169.

8. The plant part of claim 7, wherein said plant part is a cell, protoplast, an ovule, a meristem, an embryo, or a plant organ.

9. A tissue culture of cells obtained from the plant of claim 7, wherein said tissue culture of cells is from a tissue from the leaf, pollen, embryo, bulb, anther, flower, bud, or meristem.

10. An onion plant of variety SR 5637 or a seed, bulb, or plant part of said variety, representative seed of said variety having been deposited under NCIMB Accession No. 42170.

11. The plant part of claim 10, wherein said plant part is a cell, protoplast, an ovule, a meristem, an embryo, or a plant organ.

12. A tissue culture of cells obtained from the plant of claim 10, wherein said tissue culture of cells is from a tissue from the leaf, pollen, embryo, bulb, anther, flower, bud, or meristem.

13. A method for producing long day onion plants or seeds comprising crossing an onion plant of claim 1, with a second onion plant, and obtaining F1 seeds from said cross.

14. A method for producing long day onion plants or seeds comprising crossing an onion plant of claim 4, with a second onion plant, and obtaining F1 seeds from said cross.

15. A method for producing long day onion plants or seeds comprising crossing an onion plant of claim 7, with a second onion plant, and obtaining F1 seeds from said cross.

16. A method for producing long day onion plants or seeds comprising crossing an onion plant of claim 10, with a second onion plant, and obtaining F1 seeds from said cross.

* * * * *